United States Patent
Porée et al.

(10) Patent No.: US 11,660,019 B2
(45) Date of Patent: May 30, 2023

(54) FLOW MEASURING APPARATUS AND INHALATION APPARATUS COMPRISING THE SAME

(71) Applicant: PROTECSOM AMÉRIQUE DU NORD INC., Drummondville (CA)

(72) Inventors: Thierry Porée, Valognes (FR); Edouard Curran, Valognes (FR)

(73) Assignee: PROTECSOM AMÉRIQUE DU NORD INC., Drummondville (CA)

( * ) Notice: Subject to any disclaimer, the term of this patent is extended or adjusted under 35 U.S.C. 154(b) by 351 days.

(21) Appl. No.: 16/764,420

(22) PCT Filed: Nov. 15, 2018

(86) PCT No.: PCT/CA2018/051453
§ 371 (c)(1),
(2) Date: May 15, 2020

(87) PCT Pub. No.: WO2019/095065
PCT Pub. Date: May 23, 2019

(65) Prior Publication Data
US 2020/0352474 A1 Nov. 12, 2020

Related U.S. Application Data

(60) Provisional application No. 62/586,366, filed on Nov. 15, 2017.

(51) Int. Cl.
*A61B 5/087* (2006.01)
*G01F 1/46* (2006.01)
(Continued)

(52) U.S. Cl.
CPC ............ *A61B 5/087* (2013.01); *G01F 1/46* (2013.01); *A61M 16/0672* (2014.02); *A61M 2016/0036* (2013.01); *A61M 2206/10* (2013.01)

(58) Field of Classification Search
CPC ...... G01F 1/46; A61B 5/087; A61M 16/0672; A61M 2016/0036; A61M 2206/10
(Continued)

(56) References Cited

U.S. PATENT DOCUMENTS 5,038,773 A * 8/1991 Norlien ............... A61B 5/087
600/438
5,379,650 A * 1/1995 Kofoed ................. G01F 1/50
73/861.75
(Continued)

FOREIGN PATENT DOCUMENTS

FR 2993783 A1 1/2014

OTHER PUBLICATIONS

International Search Report of PCT/CA2018/051453; dated Jan. 31, 2019; Wang W.
(Continued)

*Primary Examiner* — Valerie L Woodward
*Assistant Examiner* — Paige Kathleen Bugg
(74) *Attorney, Agent, or Firm* — Benoit & Cote Inc.; Mathieu Miron

(57) ABSTRACT

The present document describes a flow measuring apparatus for measuring a flow through a section of an inhalation apparatus, comprising at least one set of Pitot tubes first a second Pitot tube and streamlinings extending longitudinally parallel to the Pitot tubes and the set of Pitot tubes is configured for traversing entirely a lumen which define the section of the inhalation apparatus and are respectively fluidly connected to a differential pressure sensor for measuring a difference between a stagnation pressure and a static pressure within the flow measuring apparatus.

20 Claims, 15 Drawing Sheets

(51) Int. Cl.
*A61M 16/00* (2006.01)
*A61M 16/06* (2006.01)

(58) Field of Classification Search
USPC .......................................................... 600/538
See application file for complete search history.

(56) References Cited

U.S. PATENT DOCUMENTS

| | | | |
|---|---|---|---|
| 5,817,950 A | 10/1998 | Wiklund et al. | |
| 2014/0158127 A1* | 6/2014 | Boucher | ................ A61M 11/00 |
| | | | 128/203.22 |
| 2016/0213865 A1* | 7/2016 | Poree | ........................ G01F 1/46 |

OTHER PUBLICATIONS

Supplementary European Search Report from Corresponding European Application No. 18877490.5; The Hague dated Jun. 9, 2021; Hirsch, Arthur.
English Abstract of FR2993783; Published Jan. 31, 2014.

* cited by examiner

| Apparatus configuration |||| 
|---|---|---|---|
| Top view ||||
|  |  |  |  |
| Config 1 | Config 2 | Config 3 | Config 4 |
|  |  |  |  |
| Config 5 | Config 6 | Config 7 | Config 8 |

Variation of pressure as a function of subconfigurations 1a, b, c (125 Pa)

A

Variation of pressure as a function of subconfigurations 2a, b, c (125 Pa)

B

Variation of pressure as a function of subconfigurations 3a, b, c (125 Pa)

C

A

B

FLOW MEASURING APPARATUS AND INHALATION APPARATUS COMPRISING THE SAME

CROSS-REFERENCE TO RELATED APPLICATIONS

This application is a US National Phase application under 35 USC § 371 of PCT/CA2018/051453, filed Nov. 15, 2018, which claims priority from and the benefit of U.S. Provisional Patent Application No. 62/586,366, filed Nov. 15, 2017, the specifications of which are hereby incorporated by reference in their entireties.

BACKGROUND

(a) Field

The subject matter disclosed generally relates to a flow measuring apparatus and an apparatus for measuring a nasal airflow, and more specifically, the subject matter disclosed relates to a flow measuring apparatus comprising a set of Pitot tubes longitudinally aligned and streamlined, that may be connected to a differential pressure sensor, and an apparatus for measuring a nasal airflow comprising the same.

(b) Related Prior Art

Many drugs to treat diseases such as obstructive pulmonary disease, asthma, bronchial, or the bronchiolitis, are administered by inhalation for example by means of metered dose inhalers (MDI). The inhaler uses a propellant which generates an aerosol of the substance drug or active substance.

Inhalation devices (or apparatus) commonly used in inhalation treatments often needs an inhalation chamber. The use of an inhalation chamber has long been recognized to facilitate and improve the medication in a treatment by inhalation (aerotherapy), in particular for improving the distribution of therapeutic substances (medicament) in the bronchi and reduce deposits in the airways above, where they are responsible for side effects. Indeed, in the absence of such an inhalation chamber, the coordination between the activation of the inhaler and inspiration is paramount. However, this coordination is difficult to achieve for many patients, especially in children.

The inhalation chamber defines an internal volume in which the medicament is propelled by means of an opening made in one end of the opening chamber which is fitted on the source of the drug, for example a MDI. At another end of the inhalation chamber is another opening in communication with the patient's mouth through a connection means, generally a tubular part such as a mouthpiece that the patient may insert in his/her mouth directly. It is also possible to connect a face mask on the connection means, in particular in the case of devices for young children. The drug substance is propelled as a gas in the inhalation chamber for example by pressing the MDI. When the patient inhales through the mask or mouthpiece, the drug substance is transported into the lungs of the patient by an outflow from the inhalation chamber generated by the patient's inhalation.

However, it is not easy for the patient to verify that the inspiratory flow generated was efficient enough to inhale the full dose of drug substance or that the inhalation device works correctly. For example, if the inspiratory flow is too low or too strong, effective treatment may be compromised.

Furthermore, currently, although it is possible to detect episodes of sleep apnea (complete cessation of breathing) in infants, there is no reliable way of measuring cases of hypopnea (decreased breathing) due to the too low respiratory flow rates generated in such conditions. To meet this need, a flow measuring apparatus capable of measuring very low respiratory flow rates would be required.

Inhalation devices including an inhalation chamber in which means of attesting to the good inhalation of the patient are known in the art. For example, there is an inhalation chamber in which a visible color means adjacent to an unidirectional inhalation valve moves according to the inspiratory flow. Such means provides a way to assess the passage of the inspiratory flow through the valve, however it does not measure the flow rate of inspiratory flow and eventually compare it to a reference value.

Therefore, it is an object of the present invention to provide a flow measuring apparatus which may be used for measuring the flow through a section of an inhalation apparatus. Also, it is an object of the present invention to provide an inhalation apparatus having a flow measuring apparatus for measuring more accurately and reliably very low respiratory flows through a section of the inhalation apparatus.

SUMMARY

According to an embodiment, there is provided a flow measuring apparatus for measuring a flow through a section of an inhalation apparatus, comprising:
at least one set of Pitot tubes comprising:
a first Pitot tube and a second Pitot tube, which both extend longitudinally and are parallel, the first Pitot tube comprising at least one outward opening facing a direction of the flow, and the second Pitot tube comprising at least one outward opening facing a direction opposed to the flow, wherein the at least one opening facing a direction of the flow and the at least one opening facing a direction opposed to the flow are substantially coplanar along the longitudinal axis of the first and the second Pitot tubes;
a first streamlining comprising
first and second planar surfaces joined at a first common edge to form a wedge extending longitudinally parallel to the first Pitot tube, and
at least one wedge opening aligned with and in fluid communication with the at least one outward opening of the first Pitot tube;
the first common edge and the at least one wedge opening outwardly facing a direction of the flow;
the set of Pitot tubes being configured for traversing entirely a lumen which defines the section of the inhalation apparatus; and
the first and second Pitot tube being respectively fluidly connected to a differential pressure sensor, for measuring a difference between a stagnation pressure and a static pressure within the flow measuring apparatus.

The first Pitot tube may be in contact with the second Pitot tube.

The first and the second Pitot tubes are back to back.

The flow measuring apparatus may further comprise:
a second streamlining comprising
third and fourth planar surfaces joined at a second common edge to form a wedge extending longitudinally parallel to the second Pitot tube, and at least one wedge opening aligned with and in fluid communication with the at least one outward opening of the second Pitot tube;

the second common edge and the at least one wedge opening outwardly facing a direction opposed to the flow.

The flow measuring apparatus may further comprise:
a second streamlining comprising a truncated cylindrical or ellipsoidal surface extending longitudinally parallel to the second Pitot tube, and
at least one streamlining opening aligned with and in fluid communication with the at least one outward opening of the second Pitot tube;
the at least one streamlining opening outwardly facing a direction opposed to the flow.

The flow measuring apparatus may further comprise:
a second streamlining comprising a planar surface substantially perpendicular to the flow and extending longitudinally parallel to the second Pitot tube, and
at least one streamlining opening aligned with and in fluid communication with the at least one outward opening of the second Pitot tube;
the at least one streamlining opening outwardly facing a direction opposed to the flow.

The first and the second streamlining form a unitary streamlining.

The flow measuring apparatus may further comprise a filler element to bridge a gap between the first and second Pitot tube.

The at least one outward opening facing a direction of the flow or the at least one outward opening facing a direction opposed to the flow are a radially outward opening.

In the flow measuring apparatus, one of the first and the second Pitot tube may be for measuring a stagnation pressure, and the other of the first and the second Pitot tube may be for measuring a static pressure.

The first Pitot tube may be for measuring a stagnation pressure, and the second Pitot tube may be for measuring a static pressure, or the first Pitot tube may be for measuring a static pressure, and the second Pitot tube may be for measuring a stagnation pressure.

The at least one opening facing a direction of the flow or the at least one opening facing a direction opposed to the flow may be a single opening, or two openings, or three openings, or four openings, or five openings.

The at least one opening facing a direction of the flow or the at least one opening facing a direction opposed to the flow may be a circular opening, or a slot, or an oval opening, or a square opening, or a rectangular opening, or combinations thereof.

The at least one opening facing a direction of the flow or the at least one opening facing a direction opposed to the flow may be positioned along the longitudinal axis of the first or second Pitot tubes at regular intervals.

The flow measuring apparatus may further comprise a processor, operatively connected to the flow measuring apparatus, for calculating the flow rate from the difference between a stagnation pressure and a static pressure measured with the flow measuring apparatus.

The flow measuring apparatus may further comprise a transmission means for transmitting the flow rate.

The flow measuring apparatus may further comprise a visual means to visually indicate correct use of the flow measuring apparatus, the inhalation apparatus, or both.

The one of the processor, the transmission means, and the visual means may be comprised within a housing.

The set of Pitot tubes may be removable.

According to another embodiment, there may be provided an apparatus for measuring a nasal airflow in a subject in need thereof, comprising:
the flow measuring apparatus of the present invention, configured to be positioned under a nose of the subject, and
connecting means, in fluid communication with the flow measuring apparatus.

The at least one opening facing a direction of the flow of the flow measuring apparatus may be positioned adjacent to a nostril of the nose of the subject.

The at least one opening facing a direction opposed to the flow of the flow measuring apparatus may be positioned adjacent to a nostril of the nose of the subject.

The connecting means may comprise a tube.

The connecting means may be fluidly connected to the differential pressure sensor.

The position under the nose of the subject may be provided by positioning means.

The positioning means comprises an adhesive, a nostril adapter, a nasal adapter configured to contact an external nose region, an adapter configured to contact an upper lip and/or a nasolabial sulcus, and combinations thereof.

The positioning means may be made from a flexible material.

The flexible material may be chosen from a polymer film, a fabric, a paper and combinations thereof.

The polymer film may be chosen from a polyethylene, a polypropylene, a polyacetal and an engineering plastic.

The engineering plastic may be chosen from a polyamide, a polyethylene terephthalate (PET), an elastomer and a thermoplastic elastomer.

The fabric may be chosen from a woven fabric, a knitted fabric and a nonwoven fabric.

The following terms are defined below.

The term "Pitot tube" is intended to mean a pressure measurement instrument used to measure fluid flow velocity. It is used to measure liquid, air and gas velocities in the present invention. The Pitot tube is used to measure the local velocity at a given point in the flow stream and not the average velocity in the pipe or conduit.

The term "dynamic pressure" is intended to mean the kinetic energy per unit volume of a fluid particle. In simplified cases, the dynamic pressure is equal to the difference between the stagnation pressure and the static pressure.

The term "static pressure" is intended to mean the pressure of a fluid particle on a body when the body is at rest relative to the fluid.

The term "stagnation pressure" is the static pressure at a stagnation point in a fluid flow. At a stagnation point the fluid velocity is zero and all kinetic energy has been converted into pressure energy (isentropically). Stagnation pressure is equal to the sum of the free-stream dynamic pressure and free-stream static pressure. Stagnation pressure is sometimes referred to as Pitot pressure because it is measured using a Pitot tube. Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

The expression "opening facing a direction of the flow" is intended to mean that the opening is substantially facing the flow, and is substantially perpendicular to the flow, to maximize the surface of the opening that will interact with the flow.

The expression "opening facing a direction opposed to the flow" is intended to mean that the opening is substantially opposed to the flow, and is substantially perpendicular to direction opposed to the flow, thus maximizing the surface of the opening that will be opposed to the flow.

The term "subject" is intended to mean humans and non-human mammals such as primates, and the like. In one embodiment, humans refer to adults or infants.

The expression "removable" or "removable means" is intended to mean any element that allows removable attachment of the inhalation apparatus to the subject. In one embodiment, "removable means" means a piece of material that is flexible enough to be removably attached to the subject, and rigid enough so that the piece of flexible material is held in place until sufficient force is applied to remove the means from the subject, such as an adhesive.

The expression "flexible material" is intended to mean any material capable of being bent. Examples of suitable flexible materials include polymer films comprising, polyethylene, polypropylene, polyacetals, engineering plastics [e.g., polyamides, polyethylene terephthalate (PET)], elastomers, thermoplastic elastomers, and combinations thereof, fabric (e.g., woven, knitted, or nonwoven fabric), paper, and combinations thereof.

The terms "longitudinal" or "longitudinally" is intended to mean extending in the direction of the length, in this case, of the Pitot tubes.

The term "coplanar" is intended to mean being or operating in the same plane.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
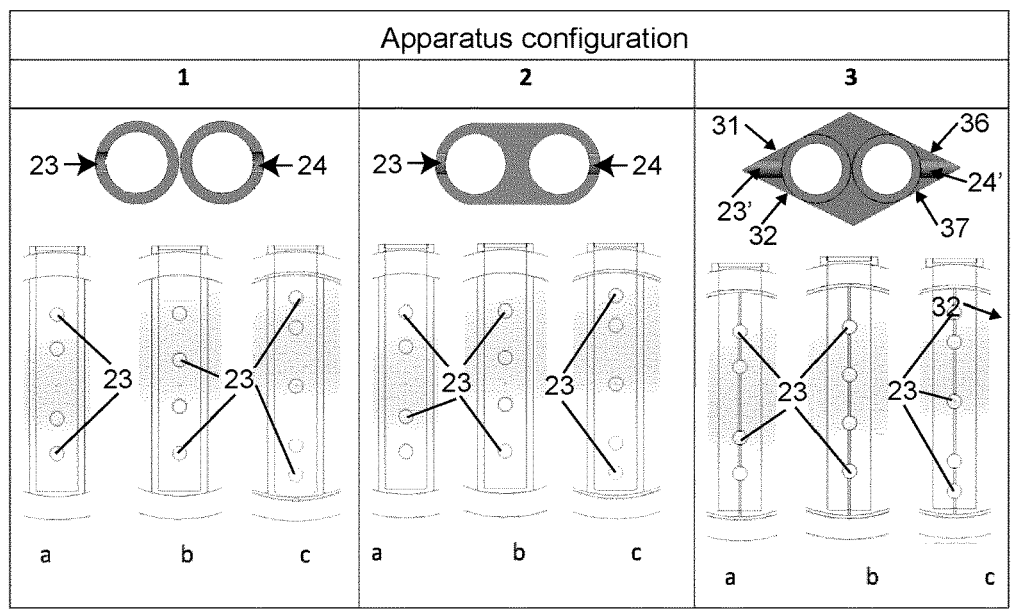
FIG. 1 illustrates top view accompanied by front view with different opening configurations of embodiments of the present invention.
Figure 2:
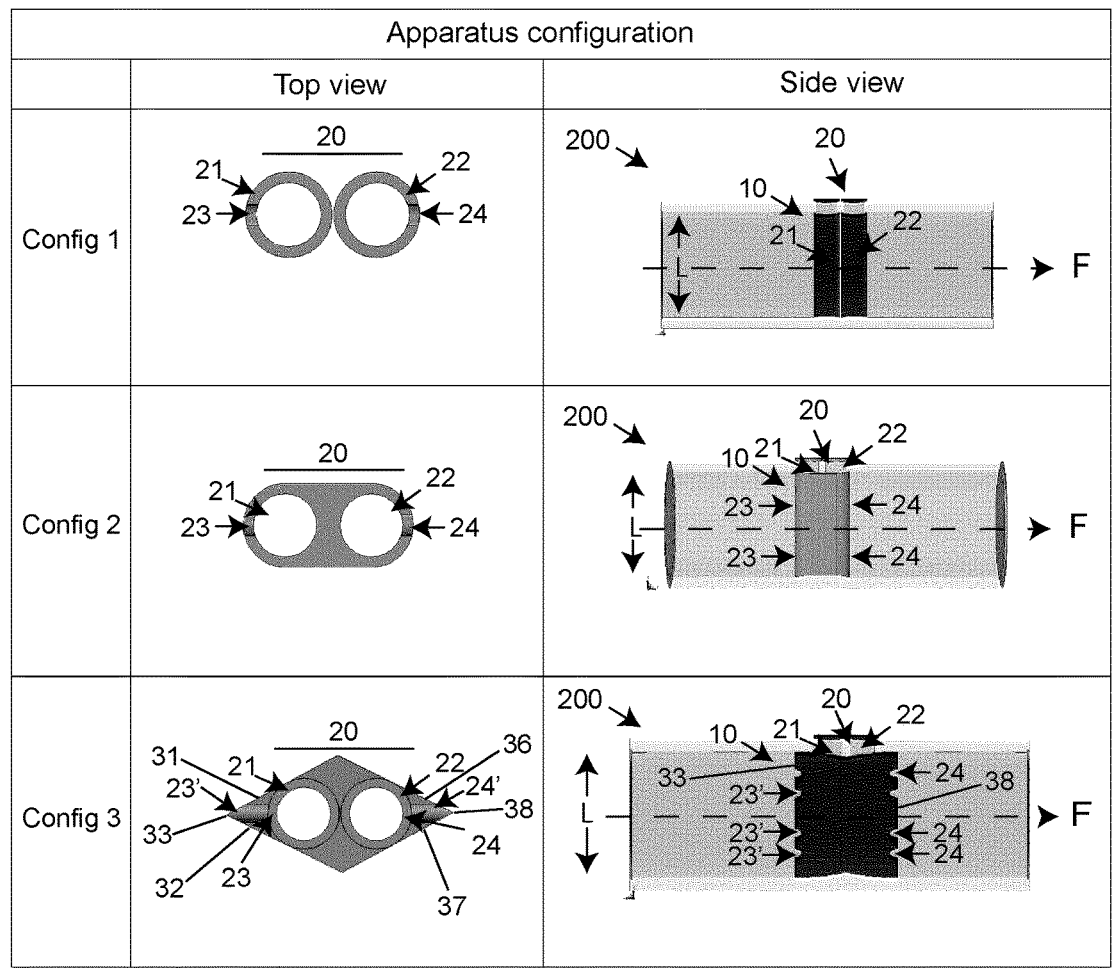
FIG. 2 illustrates top and side views of apparatuses according to embodiments of the present invention.
Figure 3:
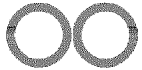
FIG. 3 illustrates top views of different configurations of embodiments of the present invention.
Figure 3:
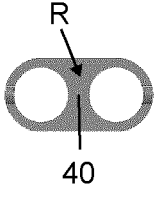
Figure 3:
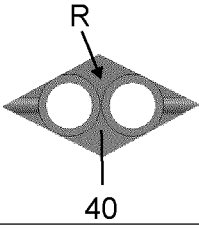
Figure 3:
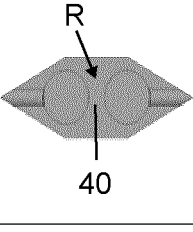
Figure 3:
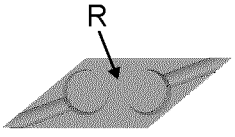
Figure 3:
Figure 3:
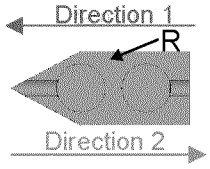
Figure 3:
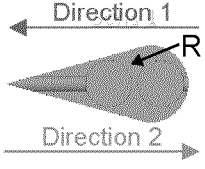

Referring now to the drawings, and more particularly to FIGS. 1-3. In a first embodiment there is disclosed a flow measuring apparatus 10 for measuring a flow (F) through a section of an inhalation apparatus 200, comprising:
 at least one set of Pitot tubes 20 comprising:
  a first Pitot tube 21 and second Pitot tube 22, which both extend longitudinally and are parallel, the first Pitot tube 21 comprising at least one outward opening 23 facing a direction of the flow, and the second Pitot tube 22 comprising at least outward one opening 24 facing a direction opposed to the flow, wherein the at least one opening facing a direction of the flow and the at least one opening facing a direction opposed to the flow are substantially coplanar along the longitudinal axis of the first and the second Pitot tubes;
  a first streamlining comprising
   first and second planar surfaces 31, 32 joined at a first common edge 33 to form a wedge extending longitudinally parallel to the first Pitot tube 21, and
   at least one wedge opening 23' aligned with and in fluid communication with the at least one outward opening 23 of the first Pitot tube 21;
   the first common edge and the at least one wedge opening outwardly facing a direction of the flow (F);
 the set of Pitot tubes being configured for traversing entirely a lumen which defines the section of the inhalation apparatus; and the first and second Pitot tube 21, 22 being respectively fluidly connected to a differential pressure sensor 324, for measuring a difference between a stagnation pressure and a static pressure within the flow (F) measuring apparatus. In embodiments, the outward openings 23 or 24 may be radially outward openings.

Figure 8:
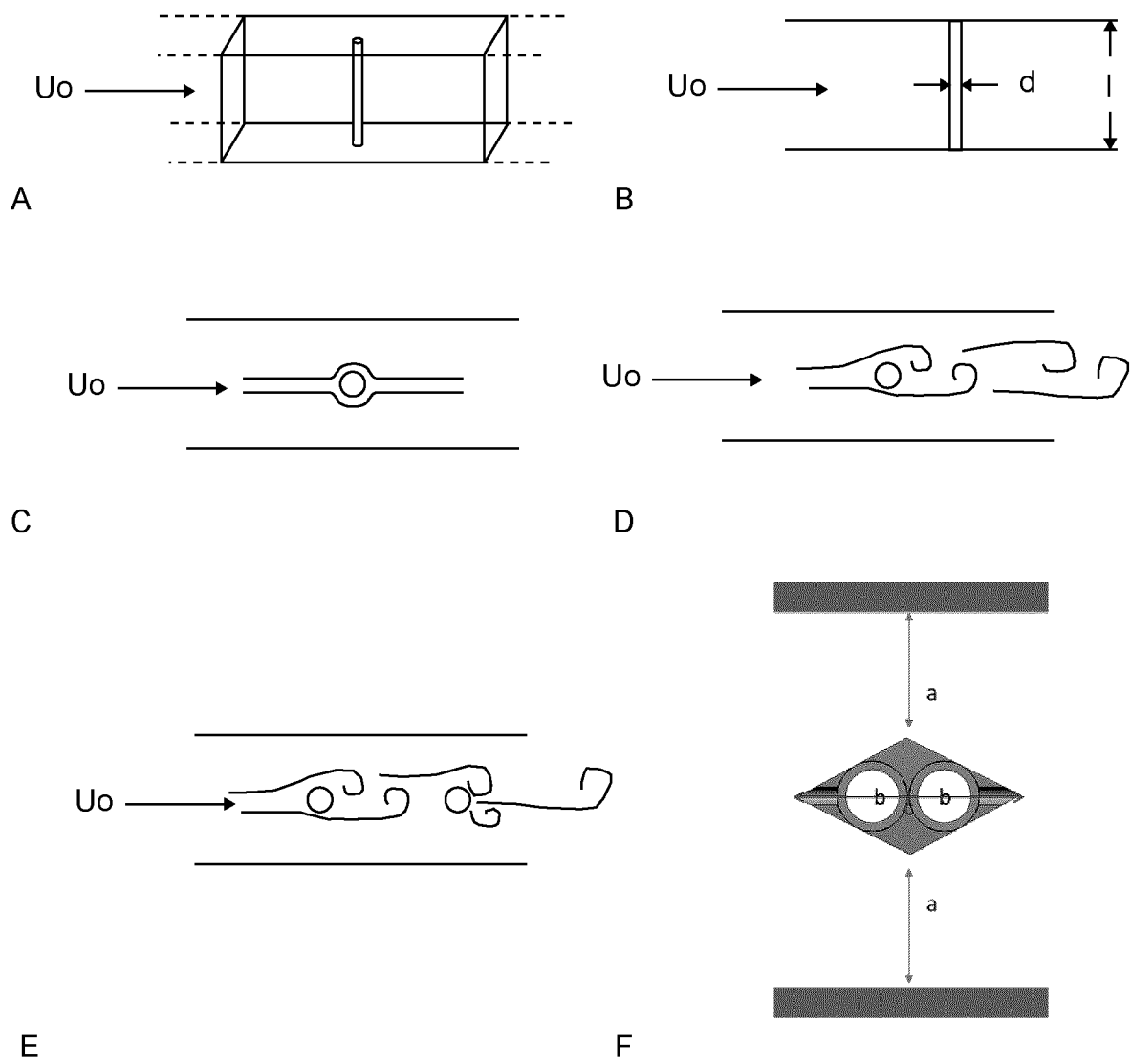
FIG. 8A illustrates schematically the flow under a scenario described herein.
FIG. 8B illustrates schematically the flow under a scenario described herein.
FIG. 8C illustrates schematically the flow under a scenario described herein.
FIG. 8D illustrates schematically the flow under a scenario described herein.
FIG. 8E illustrates schematically the flow under a scenario described herein.
FIG. 8F illustrates schematically the distance "a", diameter "b" and length "c" of an embodiment of configuration 3 according to an embodiment of the present invention.

Now referring to FIG. 8, the reference pattern usually considered as part of fluid mechanics is that of the wake formed downstream of a cylinder. The main flow in a conduit of rectangular section with sides a and b and a cylinder centered from wall to wall (diameter d and length l) (FIGS. 8A and B). The aspect ratio (l/d) of the cylinder is considered large (order of magnitude greater than 20, . . . 100).

The Reynolds number $Re=Uo.d/v$ is defined with the flow velocity $U_o$. As a function of the increase of this dimensionless number, the organization of the flow changes dramatically.

Low Reynolds numbers correspond to flow that is completely "laminar" while fully "turbulent" flows (FIGS. 8C and D, respectively) have high Reynolds number. The turbulence is extended to all parts of the flow. For Reynolds numbers ranging from 1000 to 10000 the presence of a wake is observed, where once the vortices formed in the vicinity of the downstream cylinder, they escape in alternance. The flow is essentially two-dimensional in the plane coinciding with the cylinder section. The vortices are periodic and consistent.

Other variations are discussed in the literature: the case of cylinders of small aspect ratio (short cylinders); the case where the cylinder does not cover the entire length of the test section, at the end of the cylinder, the organization of the flow becomes three-dimensional flow; and the case of tandem cylinders, where a second cylinder is placed farther downstream in the wake of the first, the organization of the flow becomes highly complex (FIG. 8E). In the case of the flow measuring apparatus 10 of the present invention, the conduit is not of rectangular section but of circular section, the flow is axy-symmetrical and not two dimensional.

Without wishing to be bound by theory, independently of the shape of the cross sections of the cylinders, they generate a wake. According to an embodiment of the present invention, the configuration of the flow measuring apparatus 10 of the present invention with a set of Pitot tubes 20 having a streamlined profile (e.g. having first and second wedges joined in a rhombus shape), traversing the entire width of the conduit (the lumen of the conduit), results in principle in a flow having an organization likely to be at least two-dimensional on the central portion of the conduit. This therefore improves the precision and the reproducibility of the measurements, especially in situations where the flow is low.

Now referring to FIGS. 2 and 3, according to an embodiment, the first Pitot tube 21 may be in contact with the second Pitot tube 22, as shown for configuration 3. According to an embodiment, the set of Pitot tubes 20 may comprise first and second Pitot tubes 21, 22 which are contacting each other along the longitudinal axis to eliminate any gap between the first and second Pitot tubes 21, 22. Now referring to FIGS. 2 and 3, in embodiments, the contact between the first and second Pitot tubes 21, 22 may be achieve in several manners. According to an embodiment, the first and second Pitot tubes 21, 22 may be back to back, resulting in their respective outward opening being substantially in the same plane (or in other words, coplanar along the longitudinal axis of the first and second Pitot tubes 21, 22), directly in contact with one another (FIG. 3, configurations 3 and 8), with or without streamlining (as shown by the filling of the region "R" in FIG. 3, configurations 2-5 and 7-8. According to another embodiment, the set of Pitot tubes 20 may be comprised of two Pitot tubes 21, 22, which are in close proximity and enclosed in a streamlining and effectively contacting each other. Preferably, the first and second Pitot tubes 21, 22 are back to back. The contact between the first and second Pitot tubes 21, 22, or the absence of a gap between them, as obtained with the presence of a streamlining, improves the precision and the reproducibility of the measurements, especially in situations where the flow is low. Furthermore, without wishing to be bound to theory, it is believed that the contact between the first and second Pitot tubes 21, 22 also reduces the turbulence in three dimensions near the flow measuring apparatus 10, limiting them to two dimensions, which again improves the precision and the reproducibility of the measurements.

Figure 4:
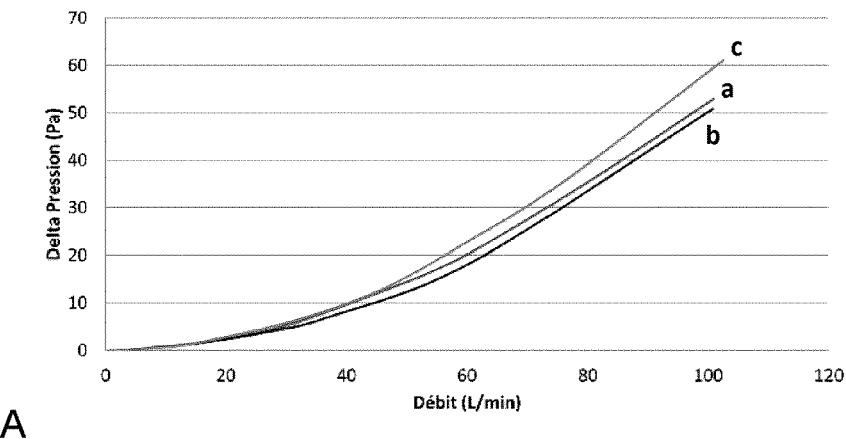
FIG. 4A illustrates the profiles of pressure as a function of flow for sub-configurations a, b and c as illustrated in FIG. 1 for configuration 1.
FIG. 4B illustrates the profiles of pressure as a function of flow for sub-configurations a, b and c as illustrated in FIG. 1 for configuration 2.
FIG. 4C illustrates the profiles of pressure as a function of flow for sub-configurations a, b and c as illustrated in FIG. 1 for configuration 3.
Figure 4:
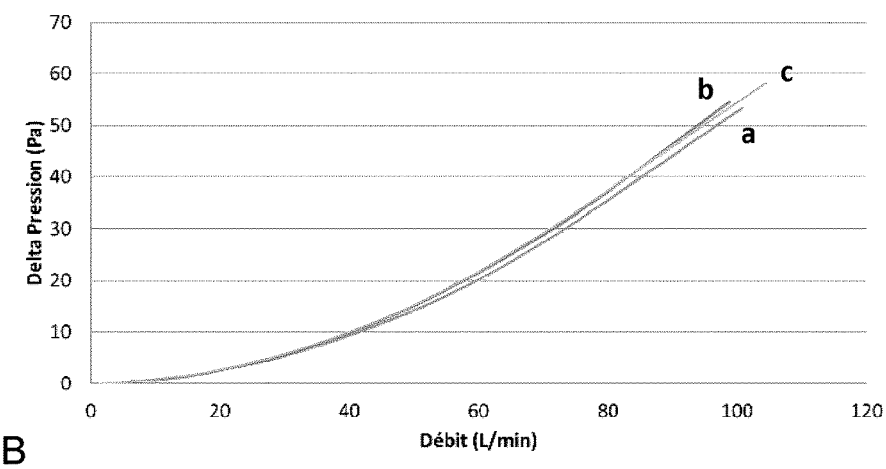
Figure 4:
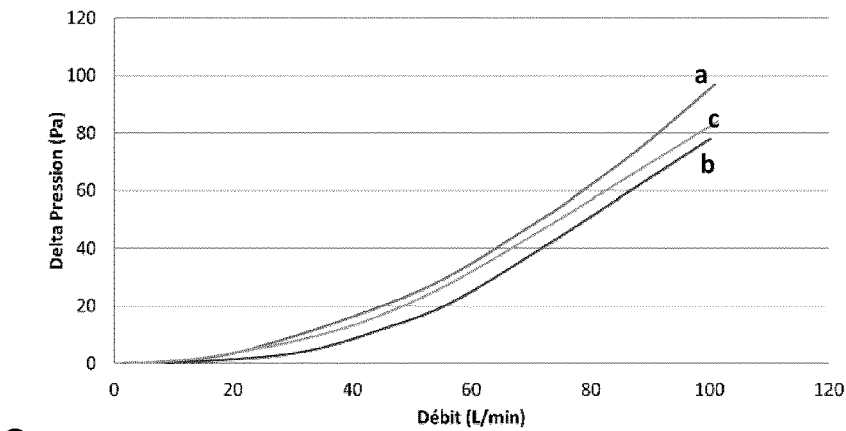

Each Pitot tube has at least one outward opening, such as outward openings 23, 24. These outward openings allow the measurement of a mean stagnation pressure and a mean static pressure during the passage of a flow through the outward openings. Thus, according to an embodiment, the first and second Pitot tubes 21, 22 may comprise at least one outward opening 23 facing a direction of the flow (F). The at least one outward opening 23 may be a single, outward longitudinal opening slot. According to another embodiment, the at least one outward opening may be two, three, four, five or more openings, such as circular openings, or slots, positioned along the longitudinal axis of the first or second Pitot tubes 21, 22 at regular intervals. According to another embodiment, the at least one outward opening is distributed along the entire length of the Pitot tube. According to another embodiment, when more than one outward openings are present, the outward openings are distributed equally (at regular intervals) along the length of the Pitot tube. Distribution along the length of the Pitot tube allows the flow to be measure at different positions in the lumen (e.g. in the center, and/or near the wall of the section of an inhalation apparatus). Now referring to FIGS. 4A-C, there is shown measurements of variation of pressures as a function of sub-configurations a, b and c (illustrated in FIG. 1), for each of configuration 1 to 3. The results presented suggest that there is no significant difference between these different sub-configurations. To facilitate the subsequent measurements, all the configurations tested were carried out with the sub-configuration "b", namely 4 holes distributed uniformly along the probe.

Now referring to FIG. 5B, which shows that the greatest pressures are at the first point of impact of the flow on the probe (i.e. apparatus of the present invention). According to the present invention, the air intake through the outward openings 23 (and 24) is preferably perpendicular to the flow. For example, for the diamond-shaped apparatus of configuration 3, the outward openings will be more effective if they are located on the edge of the diamond (i.e. as shown in configurations 3-4, and 6-8.

In embodiments, when the at least one outward opening facing a direction of the flow 23 and the at least one outward opening facing a direction opposed to the flow 24 are substantially coplanar along the longitudinal axis of the first and the second Pitot tubes 21, 22, the wedge openings 23', and 24' are also substantially coplanar along the longitudinal axis of the first and the second Pitot tubes 21, 22. See for example FIGS. 1 and 2 at configurations 3, and FIG. 3 at configurations 3-4, and 6-8.

Figure 5:
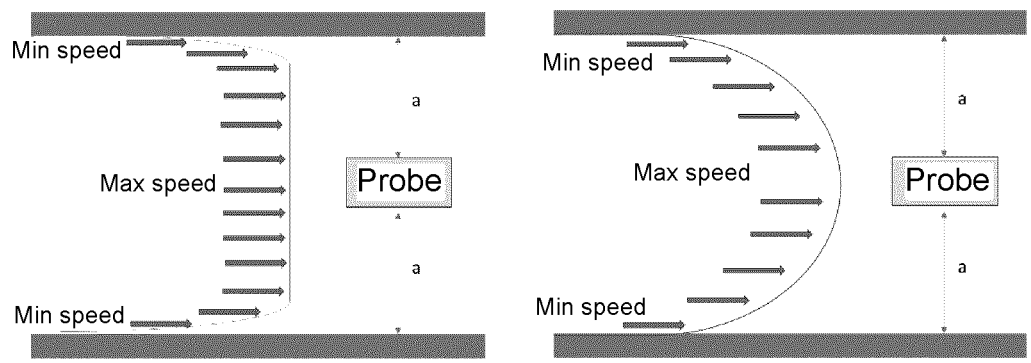
FIG. 5A is a schematic representation of a flow in turbulent (left) and laminar (right) flows. The probe is represented in the middle of the tube, separated on both sides of the walls by a distance identified as "a".
FIG. 5B illustrates the average static pressure as a function of the position of the point of impact (for a speed of 20 m/sec). From Kabaciński and Pospolita, 2008
Figure 5:
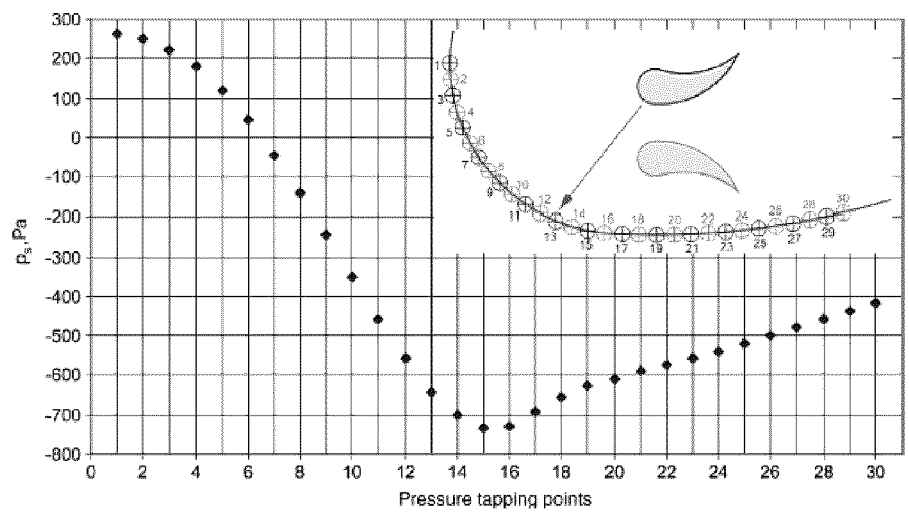

Now referring to FIG. 5, in embodiments, an object of the present invention is to have the greatest possible pressure differential, and to achieve this it is important to place the probe in the middle of the tube. In the case of a laminar or turbulent flow, the highest flow rates will be found at the center of the flow, which will allow the apparatus of the present invention to have a maximum static pressure value corresponding to the maximum flow rate of the flow (See. FIG. 5A).

Now referring to FIGS. 2 and 3. According to another embodiment, the set of Pitot tubes 20 may be streamlined in order to reduce the resistance of the set of Pitot tubes 20 to the flow within the section of an inhalation apparatus 200. According to an embodiment, the first Pitot tube is streamlined in order to reduce the resistance of the first Pitot tubes 21 to the flow within the section of an inhalation apparatus 200. According to another embodiment, both the first and second Pitot tubes may be streamlined in order to reduce the resistance of the set of Pitot tubes 20 to the flow within the section of an inhalation apparatus 200.

In embodiments, the first and second streamlining may be independent elements (e.g. FIG. 3, configuration 6), or they may form a unitary streamlining (e.g. FIG. 3, configurations 2-5 and 8). As an example, in FIG. 1, the first streamlining is comprised of first and second planar surfaces 31, 32, and the second streamlining is comprised of third and fourth planar surfaces 36, 37. Unitary streamlining may be obtained, for example, when the first and second streamlining join at the intersection of the first and third planar surfaces 31, 36 and second and fourth planar surfaces 32, 37. According to another embodiment, the Pitot tubes 21, 22 may contact each other by eliminating the region "R" between each tube, either by filling the gap between them with a filler element 40, or preparing the set of Pitot tubes 20 as a unitary part (FIG. 3, configurations 2 to 5, and 7-8). According to an embodiment, the first and second Pitot tubes 21, 22 may be inserted into another wedge shape tube, which then provides the desired streamlining (i.e. a streamlining tube). The so called streamlining tube also includes wedge or streamlining opening 23', 24' aligning with the outward openings 23, 24 of the Pitot tubes. According to another embodiment, the set of Pitot tubes 20 may be made from a unitary piece of material prepared from techniques such as injection molding, 3D printing, or machining. The unitary piece may be streamlined according to the present invention and include therein two longitudinal tube-like cavity corresponding to Pitot tubes 21, 22. Appropriate materials include but are not limited to plastic materials, metallic materials, etc.

According to embodiments, the first streamlining comprises first and second planar surfaces 31, 32 joined at the first common edge 33 to form a wedge. The angle formed by the joined first and second planar surfaces 31, 32 at edge 33 is an acute angle, as shown in configurations 3-4, 6-8, that forms the desired wedge. The angle may be in the range of from about 30° to 60°, or about 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, and 60°. Without wishing to be bound by theory, the different configurations tested support the notion that a wide range of acute angle are suitable to achieve the unexpected improvement in pressure measurements. Referring to FIG. 8F, the current shape of configuration 3 can be defined by three important elements: 1) the distance "a" should be as large as possible to avoid increasing the resistance of the airflow, particularly for apparatuses to be used with patients already having difficulty breathing; 2) the diameter "b" should be close enough to the diameter of the sensor to which the apparatus is connected, to avoid too much disturbance of the flow of air between the sensor and the apparatus, and 3) the lengths "c", the shorter the apparatus, the easier it can be inserted into different ventilation circuits.

According to embodiments, the second streamlining comprises third and fourth planar surfaces 36, 37 joined at the first common edge 38 to form a wedge. The angle formed by the joined third and fourth planar surfaces 36, 37 at edge 33 is an acute angle, as shown in configurations 3-4, and 6, that forms the desired wedge. The angle may be in the range of from about 30° to 60°, or about 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, and 60°. Without wishing to be bound by theory, the different configurations tested support the notion that a wide range of acute angle are suitable to achieve the unexpected improvement in pressure measurements. Referring to FIG. 8F, the current shape of configuration 3 can be defined by three important elements: 1) the distance "a" should be as large as possible to avoid increasing the resistance of the airflow, particularly for apparatuses to be used with patients already having difficulty breathing; 2) the diameter "b" should be close enough to the diameter of the sensor to which the apparatus is connected, to avoid too much disturbance of the flow of air between the sensor and the apparatus, and 3) the lengths "c", the shorter the apparatus, the easier it can be inserted into different ventilation circuits.

According to embodiments, the second streamlining may comprise a truncated cylindrical or ellipsoidal surface extending longitudinally parallel to the second Pitot tube 22. Such configuration is exemplified in Configuration 8, and comprises at least one streamlining opening 24' aligned with and in fluid communication with the at least one outward opening 24 of the second Pitot tube 22 and the at least one streamlining opening 24' outwardly facing a direction opposed to the flow.

According to another embodiment, the second streamlining comprising a planar surface substantially perpendicular to the flow and extending longitudinally parallel to the second Pitot tube 22. Such a configuration is exemplified in Configuration 7 and comprises at least one streamlining opening 24' aligned with and in fluid communication with the at least one outward opening 24 of the second Pitot tube 22, the at least one streamlining opening 24' outwardly facing a direction opposed to the flow.

According to another embodiment, one of the first and the second Pitot tube 21, 22 is for measuring a stagnation pressure, and the other of the first and the second Pitot tube 21, 22 is for measuring a static pressure. In an embodiment, the first Pitot tube 21 may be for measuring a stagnation pressure, and the second Pitot tube 22 is for measuring a static pressure, or the first Pitot tube 21 is for measuring a static pressure, and the second Pitot tube 22 is for measuring a stagnation pressure.

According to another embodiment, the set of Pitot tubes 20 is configured for traversing entirely the lumen (L) of the section of an inhalation apparatus 200, as shown in FIG. 2. Fluid flowing through a tubular structure flows more rapidly in the center of the structure than around the edges of the structure. Therefore, the fact that the set of Pitot tubes 20 transversely traverses the entire lumen (L) of the section of the inhalation apparatus 200, combined with having a single outwardly facing longitudinal slot, or a series of several outward openings at regular intervals along the length of the first or second Pitot tubes 21, 22, allows the measurements of the pressure to be made at several points of the lumen (L), particularly in the center and at the edges of the lumen, and permits averaging the pressure measurement and improves the precision and the reproducibility of the measurements, especially under low flow.

Figure 9:
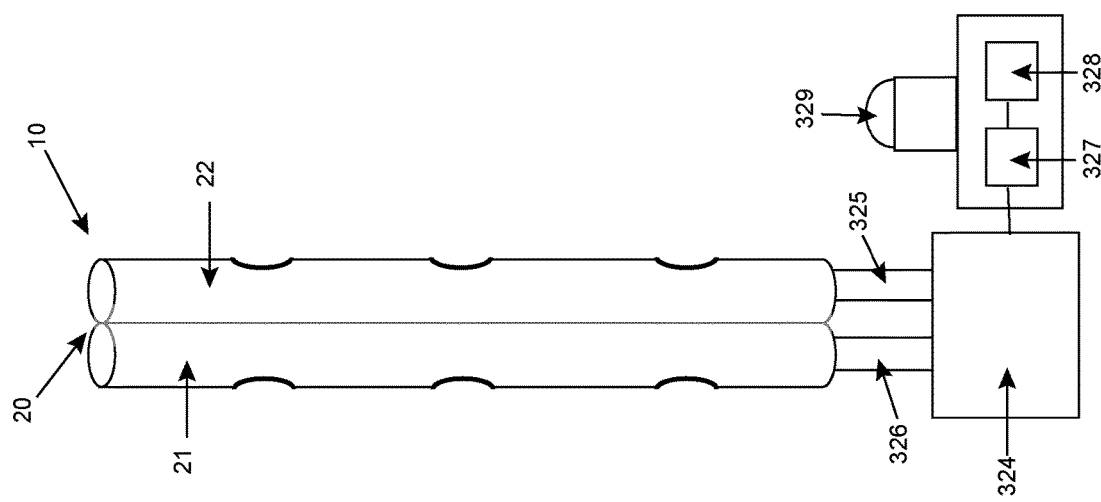
FIG. 9 illustrates an embodiment of a flow measuring apparatus according to an embodiment of the present invention.

Now referring to FIG. 9 (shown without the stream linings), according to another embodiment, the first and second Pitot tube 21, 22 are respectively fluidly connected to a differential pressure sensor 324, for measuring a difference between a stagnation pressure and a static pressure within the flow measuring apparatus 10.

The first and second Pitot tubes 21, 22 may be connected to the differential pressure sensor 324 through connecting means 325 and 326. According to another embodiment, the flow measuring apparatus 10 may also include a processor 327, for calculating the flow from the difference between a stagnation pressure and a static pressure measured with the flow measuring apparatus 10. The processor 327 may transmit a flow rate signal through transmission means 328 and/or activate visual means 329, such as a light emitting diode, or a display, indicating the correct use of an inhalation apparatus, such as apparatus 200. The operation of these elements is described in FIG. 9.

The differential pressure sensor 324, the processor 327, the transmission mean 328 and visual means 329 may be contained within a single housing. The Housing may be removably attached on the outer face of an inhalation apparatus 200. For example, it may be removable attached through connection means, such as a snap connection means. According to another embodiment, the flow measuring apparatus 10 may be totally separable from the other elements of the inhalation apparatus 200, making it easier to clean the latter. According to another embodiment, the set of Pitot tube 20 may be removable to be replaced with a fresh part, or to be cleaned.

According to another embodiment, portions of the inhalation apparatus 200 may be removable, for example to be cleaned or to be replaceable by a fresh part.

The same flow measuring apparatus 10 can comprise more than one sets of Pitot tubes 20. According to another embodiment, a flow measuring apparatus 10 of the present invention may be provided in an inhalation apparatus 200 without inspiratory or expiratory valves.

Figure 10:
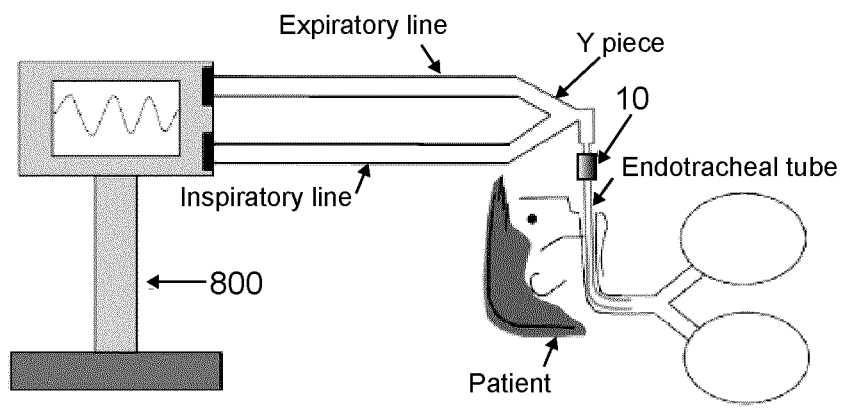
FIG. 10 illustrates schematically the use of an inhalation apparatus according to an embodiment of the present invention in a ventilation circuit.
Figure 11:
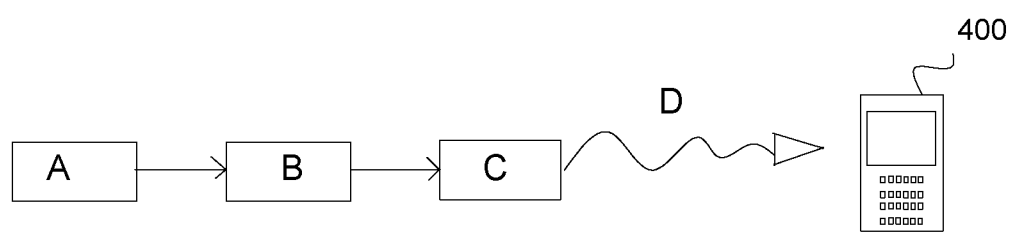
FIG. 11 illustrates schematically the functioning of an inhalation apparatus according to an embodiment of the present invention.

Now referring to FIG. 10, according to another embodiment, the flow measuring apparatus 10 of the present invention may be provided in the ventilation circuit of a ventilator 800, allowing the medical practitioner to have independent data to compare to the data of the ventilator.

In a second embodiment there is disclosed an inhalation apparatus 200 for drug delivery by inhalation comprising:
  an inhalation chamber having a first end to be connected to a source of drug to be administered by inhalation to a user (for example tubing or channel), and a second end to be connected to the user;
  a flow measuring apparatus 10 of the present invention, traversing entirely a lumen of a section of the inhalation apparatus 200, for measuring the drug flow within the section of the inhalation apparatus 200; and
  a processor 327, operatively connected to the flow measuring apparatus, for calculating the flow rate from the difference between a stagnation pressure and a static pressure measured with the flow measuring apparatus 10.

According to the second embodiment, the inhalation chamber having a first end to be connected to a source of drug is intended to be the source of drug (in other words medicinal substances or medicaments) such as a spray inhaler or metered dose inhaler (MDI), and a second end, such as a connecting portion to be connected to the user. This allows the communication between the inhalation chamber of the inhalation apparatus 200 and thus a user. According to an embodiment, the second end, such as the connecting portion may be either a mouthpiece or a tube that may be connected to a face mask.

According to another embodiment, the inhalation apparatus 200 may comprise a valve, for example a duckbill valve may be provided upstream of the user relative to the chamber. Any suitable valve may be used in the inhalation apparatus of the present invention. According to an embodiment, this valve is preferably a one-way inhalation valve allowing the passage of a flow carrying the drug particles from the interior of the chamber towards the connecting portion of the second end and the user during the inhalation phase generated by the user.

According to another embodiment, the second end may also comprises a tubular portion, having an expiratory valve. Preferably, the expiratory valve is a unidirectional valve. The expiratory valve permits the passage of the air flow generated by the user during an expiration phase to an outlet included in the tubular portion.

The inhalation apparatus 200 includes a flow measuring apparatus 10 of the present invention, traversing entirely a lumen of a section of the inhalation apparatus 200, for measuring flow of the drug within the section of the inhalation apparatus 200. The flow measuring apparatus 10 as described above may be arranged in the path of flow in the second end downstream of the valve, and/or upstream of the valve in the inhalation chamber of the inhalation apparatus 200, and/or on the expiratory flow path through the tubular portion.

Now referring to FIG. 9, the first and second Pitot tubes 21, 22 may be connected to the differential pressure sensor 324 through connecting means 325 and 326. According to another embodiment, the flow measuring apparatus 10 may also include a processor 327, for calculating the flow from the difference between a stagnation pressure and a static pressure measured with the flow measuring apparatus 10. The processor 327 may transmit a flow rate signal 328 and/or a activate visual means 329, such as a light emitting diode, indicating the correct use of an inhalation apparatus, such as apparatus 200. The operation of these elements is described in FIG. 9.

Now referring to FIG. 9, the difference between the static pressure and stagnation pressure average which are detected by the first and second Pitot tubes 21, 22 in the section of an inhalation apparatus 200 concerned is measured by the differential pressure sensor 324, which then delivers a pressure signal differential (step A). The processor 327 receives the pressure signal and calculates the flow rate (step B). The transmission means 328 transmits the signal flow delivered by the processor 327 to an external device 400, such as a portable machine equipped with a Bluetooth system or the likes (step D). This can be for example a cell phone, a tablet, etc. This allows the display on the external device 400 of either the flow value measured, or an indication to the user that a correct rate value and a proper functioning, or an incorrect rate value and an improper functioning of the inhalation apparatus 200. It is also possible to transmit a signal for the rate of drug delivery from the processor 327 to a visual means 329 attached to the inhalation apparatus 200 (step C). It may be for example a LED which illuminates when the value of the measured flow is the expected value or when on the contrary the value of the measured flow rate is less than a predetermined threshold value. This informs the user of the good operation of the inhalation apparatus 200 and the smooth running of the treatment.

The inhalation apparatus 200 may comprise a flow measuring apparatus 10 having more than one set of Pitot tubes 20. For example, a set of Pitot tubes 20 may be provided in the first end 312 of an inhalation apparatus 200 in order to measure the inhalation flow rate, and another set of Pitot tubes 20 may be provided in the tubular portion 318 that contains the expiratory valve 320 to measure the rate of expiratory flow. Also, more than one set of Pitot tubes 20 may be included in any one section of the inhalation apparatus.

According to another embodiment, a flow measuring apparatus 10 of the present invention may be provided in an inhalation apparatus 200 without inspiratory or expiratory valves.

Now referring to FIGS. 12A-F, FIGS. 13A-F, and FIGS. 16A-B according to another embodiment, there is disclosed an apparatus 1200/1300 for measuring a nasal airflow in a subject in need thereof which comprises the flow measuring apparatus 10 of the present invention, that is configured to be positioned under a nose of the subject (FIGS. 16A-B), and connecting means (such as means 56), in fluid communication with the flow measuring apparatus 10, that are in fluid communication with the differential pressure sensor 324.

Figure 16:
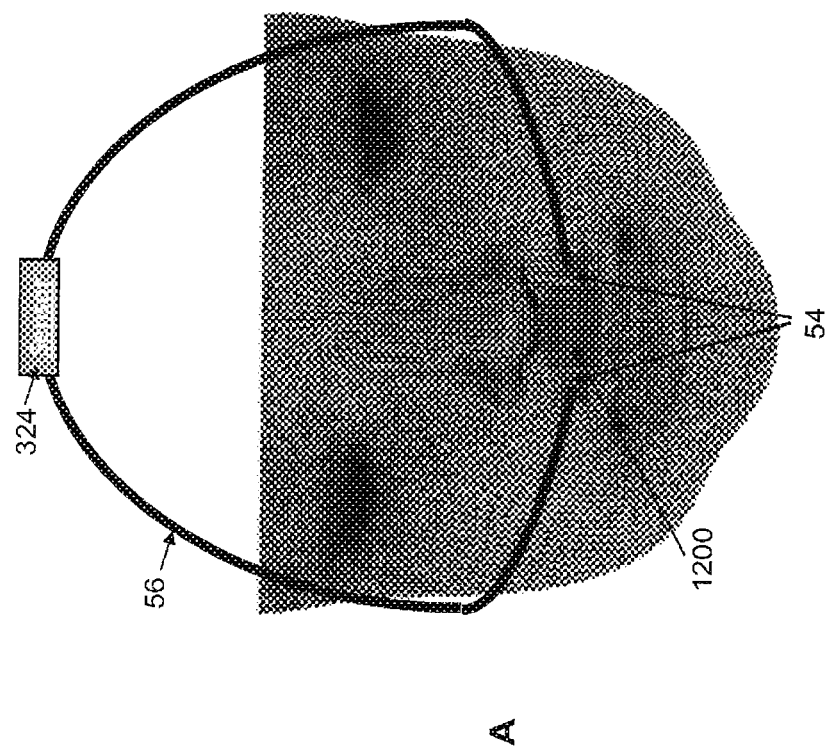
FIG. 16A illustrates a front view of an apparatus for measuring a nasal airflow according to an embodiment of the present invention in use on the face of a patient.
FIG. 16B illustrates a side view of an apparatus for measuring a nasal airflow according to an embodiment of the present invention in use on the face of a patient.
Figure 17:
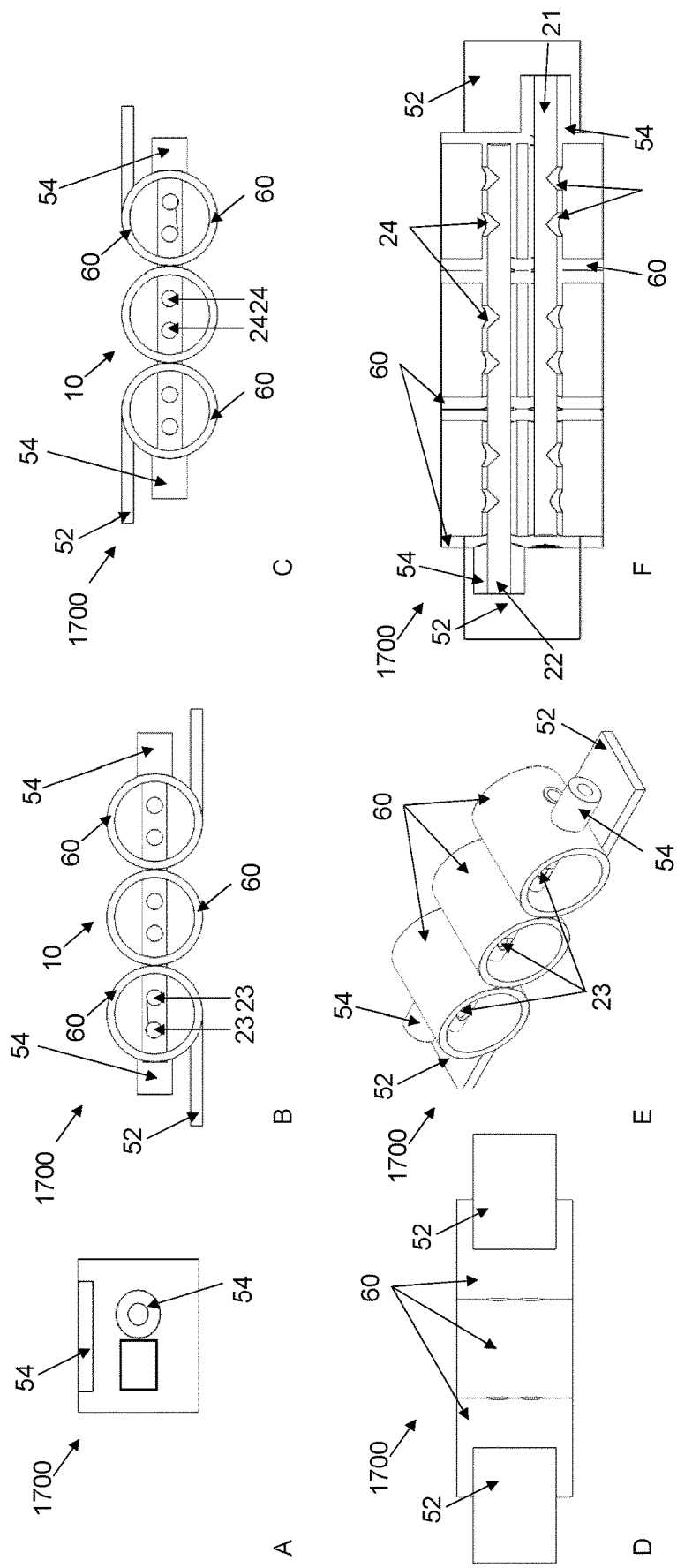
FIG. 17A illustrates a side view of an apparatus for measuring a nasal airflow, according to another embodiment of the present invention.
FIG. 17B illustrates a front view of an apparatus for measuring a nasal airflow, according to another embodiment of the present invention.
FIG. 17C illustrates a back view of an apparatus for measuring a nasal airflow, according to another embodiment of the present invention.
FIG. 17D illustrates an upper view of an apparatus for measuring a nasal airflow, according to another embodiment of the present invention.
FIG. 17E illustrates a perspective view of an apparatus for measuring a nasal airflow, according to another embodiment of the present invention.
FIG. 17F illustrates an upper cut view of an apparatus for measuring a nasal airflow, according to another embodiment of the present invention.

According to an embodiment of the apparatus for measuring a nasal airflow 1200/1300, the at least one outward opening facing a direction of the flow (shown as 23 in FIGS. 12B and E-F, and FIGS. 13B and E-F) of the flow measuring apparatus is positioned adjacent to a nostril of the nose of the subject (FIGS. 16A-B). In another embodiment, the least one outward opening facing a direction opposed to the flow (shown as 24 in FIGS. 12C and F and 13C and F) of the flow measuring apparatus 10 is positioned adjacent to a nostril of the nose of the subject; that is the apparatus 1200/1300 may be reversible. The apparatus 1200/1200 of the present invention may comprise a positioning means 52, to position the apparatus underneath the nose of the subject.

According to an embodiment, the positioning means 52 may comprise for example an adhesive, a nasal adapter configured to contact an external nose region, such as the tip of the nose, around the nostrils, the bridge of the nose, or other parts, or the entire external nose; an adapter configured to contact an upper lip and/or a nasolabial sulcus, a nostril adapter(e.g. to be inserted in a removable fashion in the nose of the patient in a sealed or non-sealed manner), and combinations of all of the above. For example, FIGS. 12A-F shows means 52 in the form of a longitudinal bar, configured to contact the upper lip of the subject. The positioning means may be removable.

In embodiments, the positioning means may be made from a flexible material, such as for example a polymer film, a fabric, a paper and combinations thereof. The polymer film may be chosen from a polyethylene, a polypropylene, a polyacetal and an engineering plastic. The engineering plastic may be chosen from a polyamide, a polyethylene terephthalate (PET). The fabric may be chosen from a woven fabric, a knitted fabric and a nonwoven fabric.

According to an embodiment, the connecting means 56 may comprise a tube. For example, flexible polymer tubing used in apparatuses for the gaseous administration of therapeutic substances would be suitable for such purpose. According to an embodiment, the connecting means 56 may be inserted, for example as illustrated in FIGS. 12A-F, 13A-F and 17A-F, in connecting ports 54, which are in fluid communication with the Pitot tubes 21, 22.

According to another embodiment, connecting means 56 may be fluidly connected to the differential pressure sensor 324, for measuring a difference between a stagnation pressure and a static pressure within the flow measuring apparatus 10. The differential pressure sensor 324 may be positioned, for example, at the extremity of the connecting means 56, and may be configured to rest behind the head of the subject, on top of the head of the subject, or any place where it may be convenient to dispose it in the context of the use scenario of the present invention.

Figure 12:
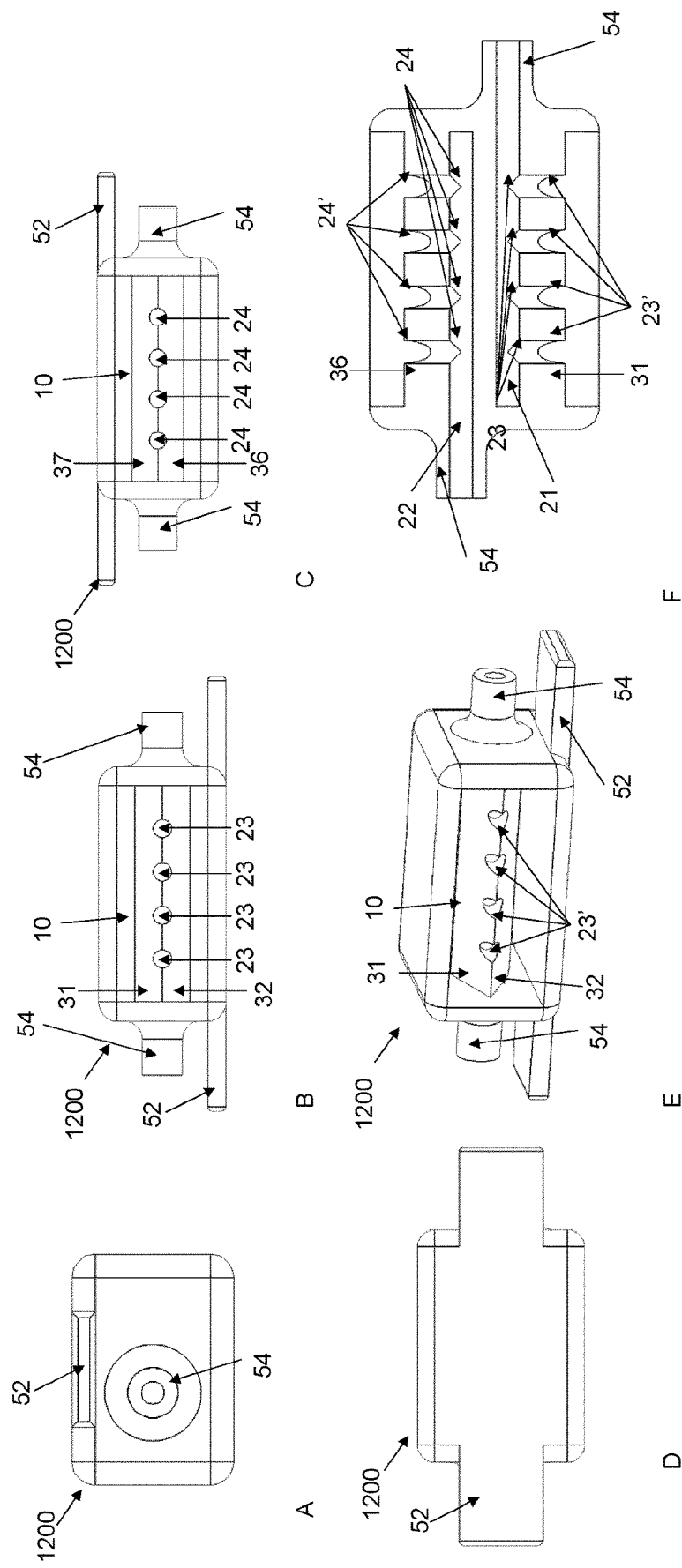
FIG. 12A illustrates a side view of an apparatus for measuring a nasal airflow, according to an embodiment of the present invention.
FIG. 12B illustrates a front view of an apparatus for measuring a nasal airflow, according to an embodiment of the present invention.
FIG. 12C illustrates a back view of an apparatus for measuring a nasal airflow, according to an embodiment of the present invention.
FIG. 12D illustrates an upper view of an apparatus for measuring a nasal airflow, according to an embodiment of the present invention.
FIG. 12E illustrates a perspective view of an apparatus for measuring a nasal airflow, according to an embodiment of the present invention.
FIG. 12F illustrates an upper cut view of an apparatus for measuring a nasal airflow, according to an embodiment of the present invention.
Figure 13:
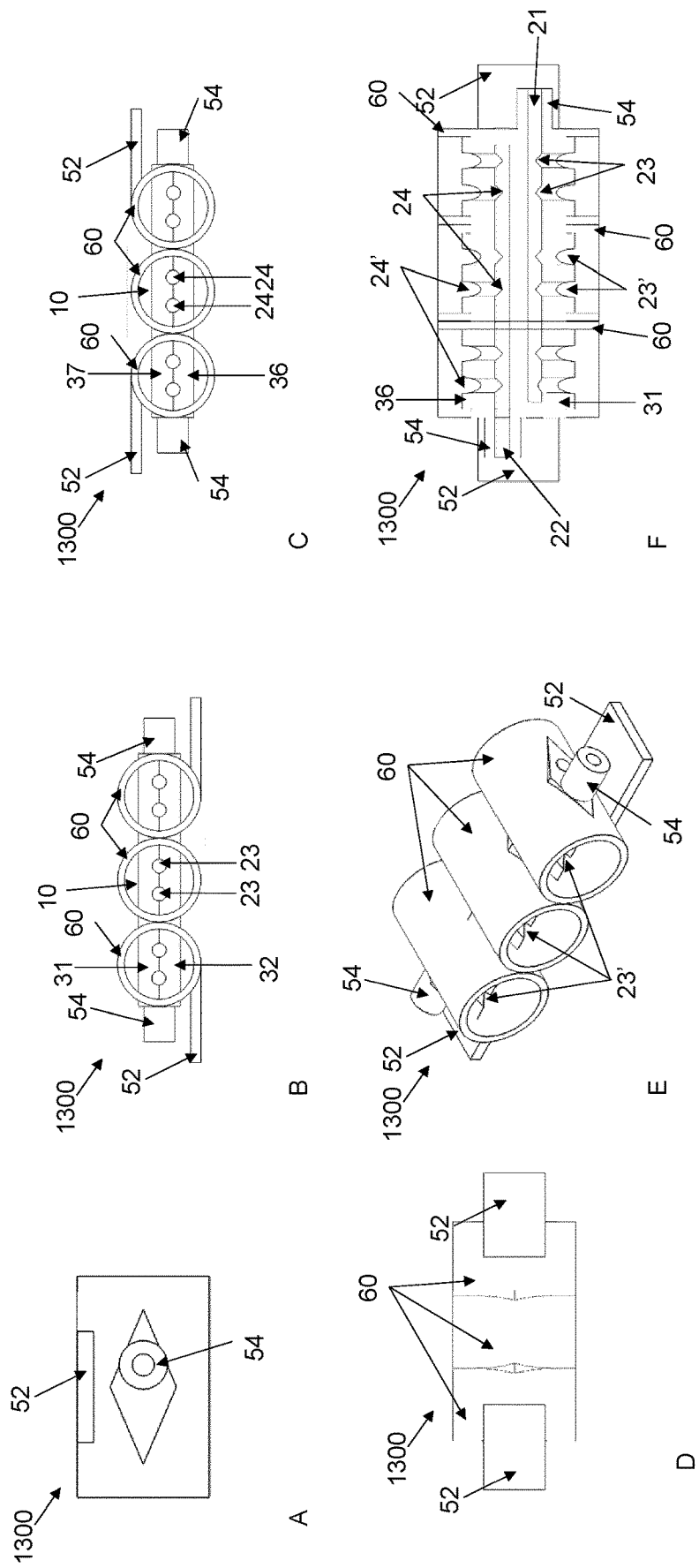
FIG. 13A illustrates a side view of an apparatus for measuring a nasal airflow, according to an embodiment of the present invention.
FIG. 13B illustrates a front view of an apparatus for measuring a nasal airflow, according to an embodiment of the present invention.
FIG. 13C illustrates a back view of an apparatus for measuring a nasal airflow, according to an embodiment of the present invention.
FIG. 13D illustrates an upper view of an apparatus for measuring a nasal airflow, according to an embodiment of the present invention.
FIG. 13E illustrates a perspective view of an apparatus for measuring a nasal airflow, according to an embodiment of the present invention.
FIG. 13F illustrates an upper cut view of an apparatus for measuring a nasal airflow, according to an embodiment of the present invention.
Figure 14:
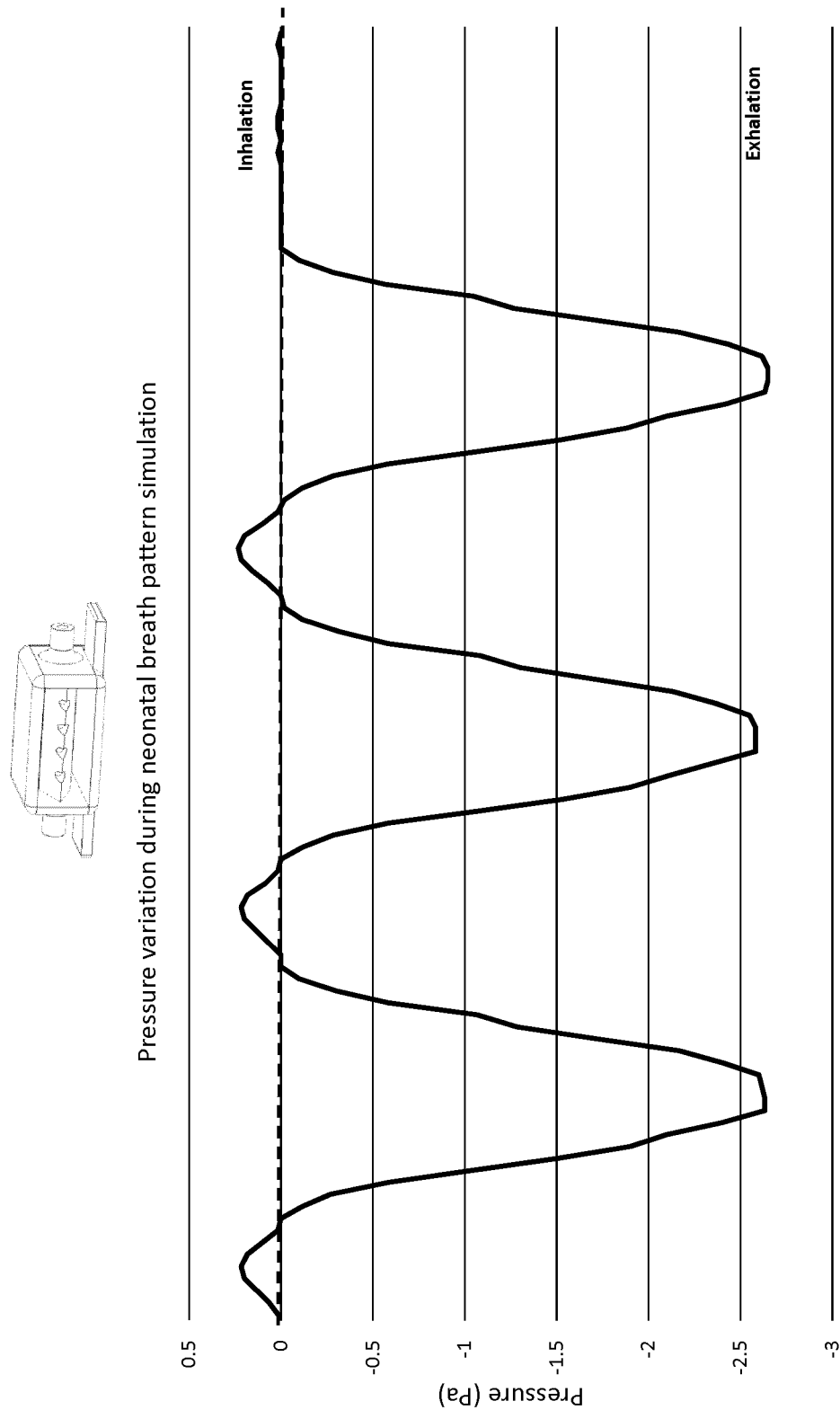
FIG. 14 illustrates the simulated pressure variation during neonatal breath pattern simulation, which shows that the present invention illustrated in FIG. 12 can detect a pressure variation within the pitot tubes even for weak respiratory profiles (here breathing of a newborn).
Figure 15:
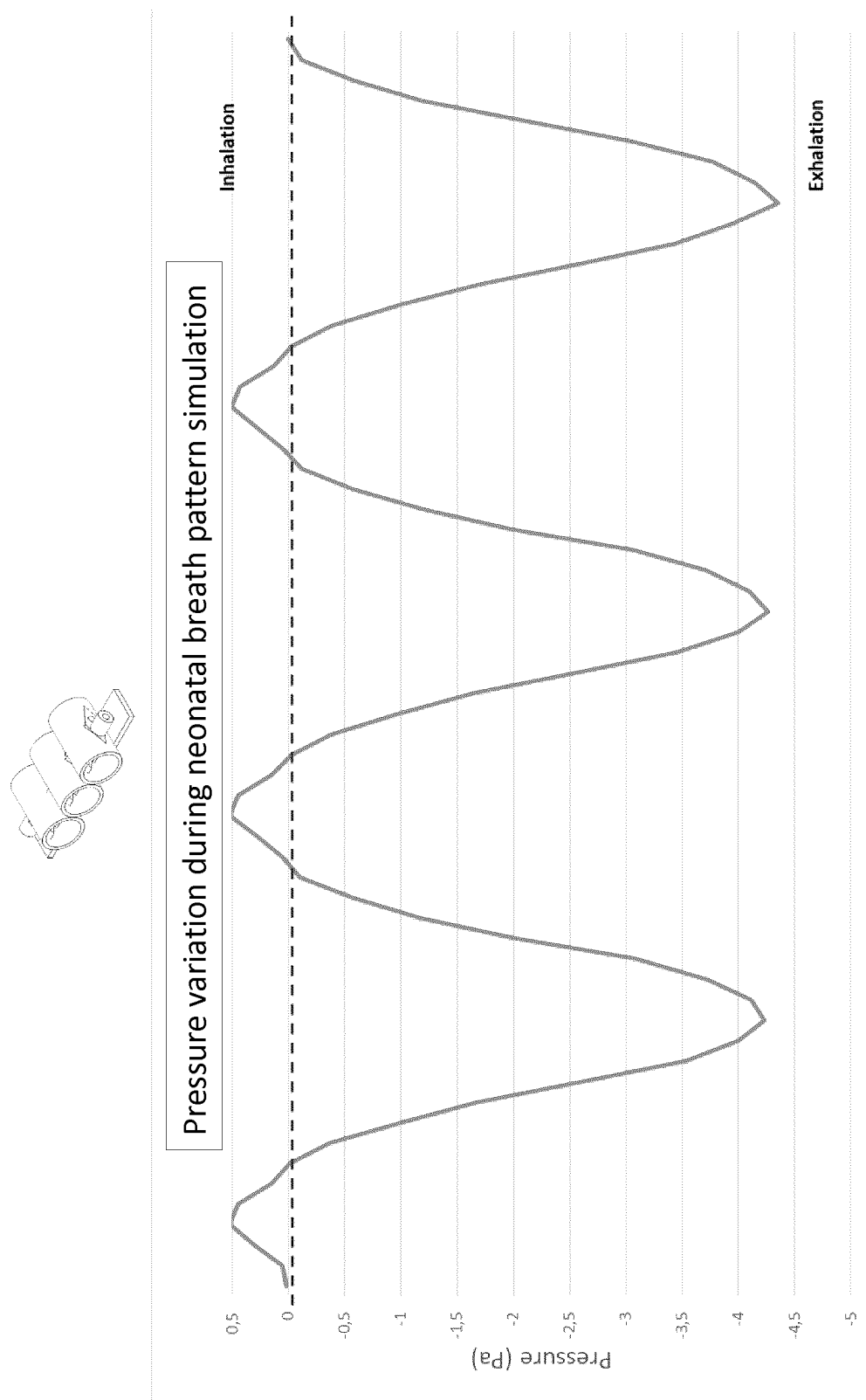
FIG. 15 illustrates the simulated pressure variation during neonatal breath pattern simulation, which shows that the present invention illustrated in FIG. 13 can detect a pressure variation within the pitot tubes even for weak respiratory profiles (here breathing of a newborn).

Now referring to FIGS. 14 and 15, these figures illustrate, for the apparatuses of FIGS. 12 and 13, the simulated pressure variation during neonatal breath pattern simulation. This shows that the present invention illustrated in FIGS. 12 and 13 can detect a pressure variation within the pitot tubes even for weak respiratory profiles (here breathing of a newborn).

Now referring to FIGS. 17A-F, according to another embodiment, there is disclosed an apparatus 1700 for measuring a nasal airflow in a subject in need thereof which comprises the flow measuring apparatus 10 of the present invention avoid no streamlining, that is configured to be positioned under a nose of the subject (FIGS. 17A-B), and connecting means (such as means 56), in fluid communication with the flow measuring apparatus 10, that are in fluid communication with the differential pressure sensor 324. The apparatus 1700

In embodiments, the at least one outward opening facing a direction of the flow (shown as 23 in FIGS. 17B and E-F) of the flow measuring apparatus is positioned adjacent to a nostril of the nose of the subject. In another embodiment, the least one outward opening facing a direction opposed to the flow (shown as 24 in FIGS. 17C and F) of the flow measuring apparatus 10 is positioned adjacent to a nostril of the nose of the subject; that is the apparatus 1700 may be reversible. The apparatus 1700 of the present invention may comprise a positioning means 52, to position the apparatus underneath the nose of the subject.

According to an embodiment, the positioning means 52 may comprise for example an adhesive, a nasal adapter configured to contact an external nose region, such as the tip of the nose, around the nostrils, the bridge of the nose, or other parts, or the entire external nose; an adapter configured to contact an upper lip and/or a nasolabial sulcus, a nostril adapter (e.g. to be inserted in a removable fashion in the nose of the patient in a sealed or non-sealed manner), and combinations of all of the above. For example, FIGS. 17A-F shows means 52 in the form of a longitudinal bar, configured to contact the upper lip of the subject. The positioning means may be removable.

In embodiments, the positioning means may be made from a flexible material, such as for example a polymer film, a fabric, a paper and combinations thereof. The polymer film may be chosen from a polyethylene, a polypropylene, a polyacetal and an engineering plastic. The engineering plastic may be chosen from a polyamide, a polyethylene terephthalate (PET). The fabric may be chosen from a woven fabric, a knitted fabric and a nonwoven fabric.

According to an embodiment, the connecting means 56 may comprise a tube. For example, flexible polymer tubing used in apparatuses for the gaseous administration of therapeutic substances would be suitable for such purpose. According to an embodiment, the connecting means 56 may be inserted, for example as illustrated in FIGS. 17A-F, in connecting ports 54, which are in fluid communication with the Pitot tubes 21, 22.

According to another embodiment, connecting means 56 may be fluidly connected to the differential pressure sensor 324, for measuring a difference between a stagnation pressure and a static pressure within the flow measuring apparatus 10. The differential pressure sensor 324 may be positioned, for example, at the extremity of the connecting means 56, and may be configured to rest behind the head of the subject, on top of the head of the subject, or any place where it may be convenient to dispose it in the context of the use scenario of the present invention.

The apparatus exemplified in FIGS. 13A-F and 17A-F comprise guiding conduits 60 (shown therein as tubes 60), substantially perpendicular to the Pitot tubes 21, 22, that direct the flow of to the flow measuring apparatus 10. The guiding conduits may have other shapes, such as rectangular, oval, square shape.

The present invention will be more readily understood by referring to the following examples which are given to illustrate the invention rather than to limit its scope.

EXAMPLE 1

Configuration Tests

Configurations Tested

The configurations tested are shown in both FIGS. 1, 2 and 3.

Test Performed

For each configuration illustrated in FIGS. 1-3 two different tests were performed. In the first test, a computer simulation was implemented to predict the pressure differences within the different flow measuring apparatus configurations for increasing air flows from 0 to 30 L/min, for configurations 1 to 3. The second test involved making measurements in vitro in the laboratory via the use of specific sensors (Sensirion™ 125Pa) and a pump to generate the varying air flow, for each of configurations 1 to 8, where configurations 7 and 8 were tested in each of their two orientation, as they were not symmetrical along the axis perpendicular to the flow.

In these two tests, the different values collected allowed the determination of the delta P (Total pressure–Static pressure) which is then used to define the flux coefficient K according to the formulas presented in the publication of Kabaciński (Kabaciński, M., and Pospolita, J. (2011). Experimental research into a new design of flow-averaging tube. Flow Meas. Instrum. 22, 421-427). According to this calculation, a coefficient K that is as weak and stable as possible despite changes in speed is preferred. In fact, it is important to have a pressure differential as large as possible and therefore a coefficient K as small and stable as possible. A high pressure differential is very important for measuring gases having a low velocity.

Results

Analysis of the Flux Coefficient K

Figure 6:
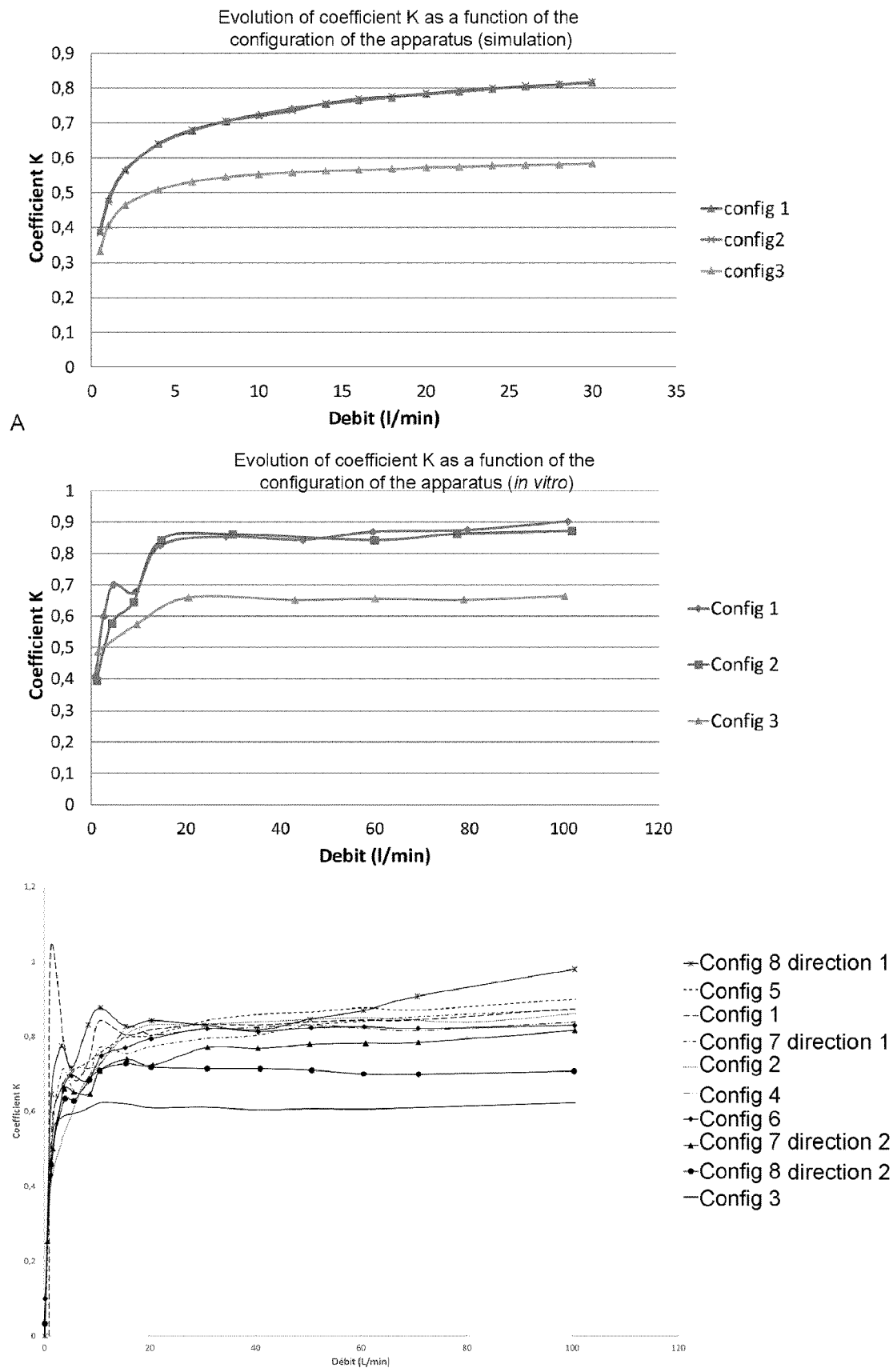
FIG. 6A illustrates the simulated evolution of the coefficient K as a function of the configuration 1, 2 or 3 tested.
FIG. 6B illustrates the in vitro measured evolution of the coefficient K as a function of the configuration 1, 2 or 3 (top) tested and as a function of configurations 1 to 8 tested (bottom).

The different configurations are compared in order to verify the impact of the shape of this probe on the variation of the coefficient K. Now referring to FIGS. 6A and B, the analysis shows that in the two tests carried out, configuration 3 unexpectedly has a coefficient K which stabilizes at a lower value (0.6-0.65) than for configurations 1 and 2 (0.8-0.9), with configurations 5 and 8 (direction 1) performing worse than the baseline configuration 1. Assymetric apparatuses 7 and 8 perform well when oriented in direction 2, but not in direction 1, which opposes a greater obstacle to the flow, although configuration 7 direction 1 does perform better than baseline configuration 1. Indeed, the results of a flow in the opposite direction (Direction 1, FIG. 3) are clearly less favorable, which may be a concern when the flux changes generated by the alternation between inspiration and expiration.

Analysis of the Pressure Difference (Delta P)

Figure 7:
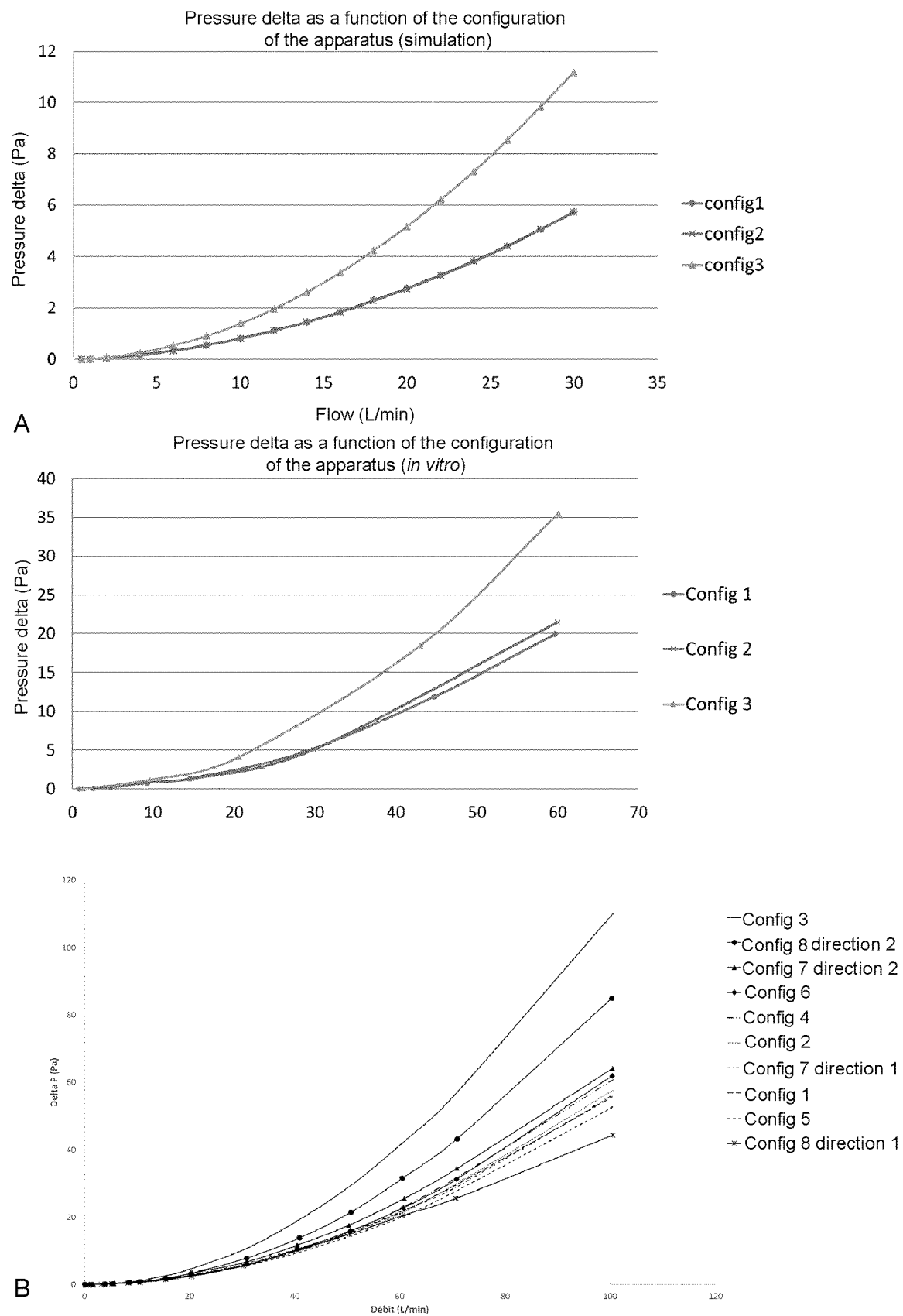
FIG. 7A illustrates the simulated pressure delta as a function of the configuration 1, 2 or 3 tested.
FIG. 7B illustrates the measured in vitro pressure delta as a function of the configuration 1, 2 or 3 (top) tested and as a function of configurations 1 to 8 tested (bottom).

Now referring to FIGS. 7A and B, the differences in pressures as a function of the flow is illustrated, and the impact of the different configurations on the profiles obtained is observed.

The results show that configuration 3 makes it unexpectedly possible to have a pressure difference (delta P) greater than that obtained for the other configurations for values of the same flow rate. For example, for a flow rate of 30 L/min, the delta P of configurations 1 and 2 is 5 Pa whereas it is 10 Pa for configuration 3. Again configurations 5 and 8 (direction 1) perform worse than the baseline configuration 1. Assymetric apparatuses 7 and 8 perform well when oriented in direction 2, but not in direction 1, which opposes a greater obstacle to the flow, although configuration 7 direction 1 does perform better than baseline configuration 1.

Conclusion

These results emphasize that the configuration 3 of the flow measuring apparatus allows the measurement of pressure deltas greater than the other configurations tested. If these different configurations are classified according to their performances in these two tests, the results are (from best to worse): Configuration 3>Configuration 8 direction 2>Configuration 7 direction 2>Configuration 6>Configuration 4>Configuration 2>Configuration 7 direction 1>Configuration 1>Configuration 5>Configuration 8 direction 1.

Since a high pressure differential is a very important parameter for measuring low velocity gases (Kabaciński and Pospolita, 2011), the use of a probe with such a configuration should make it possible to measure low respiratory flows such as those expected in the case studies of apnea and hypopnea in infants.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. An apparatus for measuring a nasal airflow in a subject in need thereof, comprising:
   a flow measuring apparatus having a section and comprising at least one set of Pitot tubes comprising:
      a first Pitot tube and a second Pitot tube, which both extend longitudinally and are parallel, said first Pitot tube comprising at least two outward openings facing a direction of said flow, and said second Pitot tube comprising at least two outward openings facing a direction opposed to said flow, wherein said at least two openings facing the direction of said flow and said at least two openings facing the direction opposed to said flow are substantially coplanar along the longitudinal axis of said first Pitot tube and said second Pitot tubes;
      a first streamlining comprising first planar surface and a second planar surfaces joined at a first common edge to form a wedge extending longitudinally parallel to said first Pitot tube, and at least one wedge opening aligned with and in fluid communication with said at least two outward openings of said first Pitot tube; said first common edge and said at least one wedge opening outwardly facing the direction of said flow;
      at least two guiding conduits substantially perpendicular to the at least one set of Pitot tubes, each of the at least two guiding conduits surrounding a corresponding one or corresponding ones of the at least two outward openings facing the direction of said flow;
      said flow measuring apparatus configured to be positioned under a nose of said subject toward which the section of the flow measuring apparatus opens, either the at least two outward openings of said first Pitot tube or the at least two outward openings of said second Pitot tube being oriented toward a nostril of said subject to measure the nasal airflow;
      said at least one set of Pitot tubes being configured for traversing entirely a lumen which defines said section of the flow measuring apparatus; and said first Pitot tube and said second Pitot tube being respectively fluidly connected to a differential pressure sensor, for measuring a difference between a stagnation pressure and a static pressure within said flow measuring apparatus.

2. The apparatus for measuring a nasal airflow of claim 1, wherein said first Pitot tube is in contact with said second Pitot tube.

3. The apparatus for measuring a nasal airflow of claim 2, wherein said first Pitot tube and said second Pitot tubes are back to back.

4. The apparatus for measuring a nasal airflow of claim 1, further comprising:
   a second streamlining comprising:
      a third planar surface and a fourth planar surfaces joined at a second common edge to form a wedge extending longitudinally parallel to said second Pitot tube, and at least one wedge opening aligned with and in fluid communication with said at least two outward openings of said second Pitot tube; said second common edge and said at least one wedge opening outwardly facing the direction opposed to said flow.

5. The apparatus for measuring a nasal airflow of claim 1, further comprising:
   a second streamlining comprising a truncated cylindrical or ellipsoidal surface extending longitudinally parallel to said second Pitot tube, and at least one streamlining opening aligned with and in fluid communication with said at least two outward openings of said second Pitot tube;
   said at least one streamlining opening outwardly facing a direction opposed to said flow.

6. The apparatus for measuring a nasal airflow of claim 1, further comprising:
   a second streamlining comprising a planar surface substantially perpendicular to said flow and extending longitudinally parallel to said second Pitot tube, and at least one streamlining opening aligned with and in fluid communication with said at least two outward openings of said second Pitot tube;
   said at least one streamlining opening outwardly facing the direction opposed to said flow.

7. The apparatus for measuring a nasal airflow of claim 4, wherein said first streamlining and said second streamlining form a unitary streamlining.

8. The apparatus for measuring a nasal airflow of claim 1, further comprising a filler element to bridge a gap between said first Pitot tube and second Pitot tube.

9. The apparatus for measuring a nasal airflow of claim 1, wherein said at least two outward openings facing the direction of said flow or said at least two outward openings facing the direction opposed to said flow are radially outward openings.

10. The apparatus for measuring a nasal airflow of claim 1, wherein one of said first Pitot tube and said second Pitot tube is for measuring a stagnation pressure, and the other of said first Pitot tube and said second Pitot tube is for measuring a static pressure.

11. The apparatus for measuring a nasal airflow of claim 1, wherein said at least two openings facing the direction of said flow or said at least two openings facing the direction opposed to said flow comprise two openings, or three openings, or four openings, or five openings;
   wherein said at least two openings facing the direction of said flow or said at least two openings facing the direction opposed to said flow each comprises a circular opening, or a slot, or an oval opening, or a square opening, or a rectangular opening, or combinations thereof;
   wherein said at least two openings facing the direction of said flow or said at least two openings facing the direction opposed to said flow is positioned along the longitudinal axis of the first Pitot tube or said second Pitot tubes at regular intervals.

12. The apparatus for measuring a nasal airflow of claim 1, further comprising a processor, operatively connected to said flow measuring apparatus, for calculating said flow rate from said difference between a stagnation pressure and a static pressure measured with said flow measuring apparatus.

13. The apparatus for measuring a nasal airflow of claim 12, further comprising any one of a transmission means for transmitting said flow rate, and a visual means to visually indicate correct use of said flow measuring apparatus, said apparatus for measuring a nasal airflow, or both.

14. The apparatus for measuring a nasal airflow of claim 1, wherein said at least one set of Pitot tubes is removable.

15. The apparatus for measuring a nasal airflow of claim 1, further comprising:
   connecting means, in fluid communication with said differential pressure sensor and with said first Pitot tube and said second Pitot tube, to respectively fluidly connect said first Pitot tube and said second Pitot tube to the differential pressure sensor.

16. The apparatus for measuring a nasal airflow of claim 1, wherein said at least two openings facing the direction of said flow of the flow measuring apparatus is positioned adjacent to a nostril of the nose of the subjects or wherein said at least two openings facing the direction opposed to said flow of the flow measuring apparatus is positioned adjacent to a nostril of the nose of the subject.

17. The apparatus for measuring a nasal airflow of claim 1, wherein positioning said flow measuring apparatus under said nose of said subject is provided by positioning means.

18. The apparatus for measuring a nasal airflow of claim 17, wherein said positioning means comprises an adhesive, a nostril adapter, a nasal adapter configured to contact an external nose region, an adapter configured to contact an upper lip and/or a nasolabial sulcus, and combinations thereof.

19. The apparatus for measuring a nasal airflow of claim 1, wherein said at least two guiding conduits are tubes.

20. The apparatus for measuring a nasal airflow of claim 19, wherein the at least two outward openings comprise six outward openings and said at least two guiding conduits further comprises a third guiding conduit, wherein each guiding conduit is a tube, with each tube surrounding two corresponding ones of the six outward openings facing the direction of said flow.

* * * * *